(12) United States Patent
Milgram et al.

(10) Patent No.: US 6,180,678 B1
(45) Date of Patent: Jan. 30, 2001

(54) USE OF ADRAFINIL TO TREAT BEHAVIORAL PROBLEMS IN AGED CANINES

(75) Inventors: William Norton Milgram, Toronto; Christina Teresa Siwak, Scarborough, both of (CA); Fredrique Woebrle-Fontaine, Lure (FR); Beth Anne Adams, Hamilton (CA); Philippe Gruet, Yvrac (FR)

(73) Assignee: Vétoquinol S.A., Lure Cedex (FR)

(*) Notice: Under 35 U.S.C. 154(b), the term of this patent shall be extended for 0 days.

(21) Appl. No.: 09/374,736

(22) Filed: Aug. 13, 1999

(51) Int. Cl.$^7$ ................................................. A61K 31/165
(52) U.S. Cl. ........................... 514/618; 514/878; 514/879
(58) Field of Search .................................. 514/618, 878, 514/879

(56) References Cited

U.S. PATENT DOCUMENTS 5,234,421 * 8/1993 Lowman ........................... 604/385.1
5,401,776 * 3/1995 Laurent ................................ 514/618

OTHER PUBLICATIONS

Benoit, O., Clodore, M., Touron, N., Pailhous, E. Effects of Modafinil on sleepiness in normal sleep deprived and symptomatic subjects, Proceedings of the 5th International Congress of Sleep Research; 1987, Jun. 28–Jul. 3; Copenhagen, Abstract book 1987.

Boyer P. (1994). Age et performance cognitives, plaintes mńesiques et attentionnelles au quotidien. Synapse n° spécial "Vers une médecine des comportements": 1–4.

Boyer P, Weil JS, Lubin S, Von Frenckell R. (1991). Inhibition de l'action et handicap idéomoteur. Résultats d'une étude controlée Adrafinil (Olmifon) versus placebo. Synapse: Dec. (n° 81).

Cian, C., Baranski, J., Esquivie, D., Raphel, C. Effets de différents dosages de modafinil sur la vigilance et les performances cognitives au cours d'une privation de sommeil de 60 heures. SSA Trav. Scient. 1997, n° 18:255–256.

Defrance D, Raharison, S, Hervé MA, Fondaraï J Bétrancourt JC, and Lubin S. Malade ages institutionnalises et Olmifon (adrafinil): determination d'un profil de "repondeurs" a l'occasion d'un "effect centre" lors d'un essai controle versus placebo. Actualit´´ Médicales Internationales Psychiatrie 1991; 8: 1815–1823.

Dewailly, P.; Durocher, A. M.; Durot, A.; Bukowski, J.V.; Frigard, B.; Herbin, H.; Lemaire, P.; Kohler, F.; Betrancourt, J. C.; Lubin, S.: Adrafinil et ralentissement du sujet age institutionnalise: de la significativite statistique a la pertinence clinique (resultat d'une etude multicentrique en double aveugle versus placebo). Actualites Medicales Internationales Psychiatrie 1989; 6: 1–8.

Duteil, J., Rambert, F.A., Pessonnier, J., Hermant, J.F., Gombert, R., Assous, E. Central alpha 1–adrenergic stimulation in relation to the behaviour stimulating effect of modafinil; studies with experimental animals. Eur. J. Pharmacol. 1990; 180:49–58.

Duteil, J., Rambert, F.A., Pessonnier, J., Gombert, R., & Assous, E. (1979). A possible–adrenergic mechanism for drug (CRL 40028)–induced hyperactivity. European Journal of Pharmacology, 59, 121–123.

Edgar, D.M., & Seidel, W.F. (1997). Modafinil induces wakefulness without intensifying motor activity of subsequent rebound hypersomnolence in the rat. Journal of Pharmacology and Experimental Therapeutics 283:757–769.

Ferner, U., Matejcek, M. & Neff, G. (1983). Confirmatory and exploratory analysis applied to pharmaco–EEGand relate study data: contradiction or useful enrichment? Neuropsychobiology, 9, 182–192.

Ferraro L, Tanganelli S, O'Connor WT, Antonelli T, Rambert F, Fuxe E. The vigilance promoting drug modafinil increases dopamine release in the rat nucleus accumbens via the involvement of a local GABAergic mechanism. *Eur J Pharmacol*, 1996; 306: 33–39.

Fontan, Fondaraï J, Micas M, Albarède J–L.: Interet de la psychometrie informatisee dans l'appreciation de l'activite d'Olmifon (adrafinil) on alertness and cognitive performance in elderly retirement home patients. *Psychologie Medicale* 1990; 22: 253–267.

Fuxe, K., Rambert, F.A., Ferraro, L., O'Connor, W., Laurent, Ph., Agnati, L.F., Tanganelli, S. Preclinical studies with modafinil. Evidence for vigilance enhancement and neuroprotection. Drugs of Today, 1996, 32(4):313–326, 32(suppl.1):7–21.

Gold, L.H.,& Baaalster, R.L. (1996). Evaluation of the cocaine like discriminative stimulus effects and reinforcing effects of modafinil. Psychopharmacology, 126, 286–292.

Guyotat J. Intérèt de l'adrafiil dans le traitement des manifestations dépressives des malades âgés. Psychologie Médicale 1987; 1901–1910.

Israel L, Fondaraï J, Lubin S, Salin B, Hugono, R. L'Adrafinil (Olmifon) et patients âgés ambulatoires. Efficacité, versus placebo, de l'Adrafinil sur l'éveil dans les activités de la vie quotidienne. *Psychologie Médicale* 1989; 21: 1235–1255.

(List continued on next page.)

Primary Examiner—Frederick Krass
(74) Attorney, Agent, or Firm—Seidel, Gonda, Lavorgna & Monaco, PC (57) ABSTRACT

A method of treating age related behavorial problems in dogs is disclosed. The method involves administering adrafinil or a metabolite thereof to an animal in need of such treatment.

18 Claims, 9 Drawing Sheets

OTHER PUBLICATIONS

Kohler F, Lubin, S. Etude en medecine generale de l'interet therapeutique d'Olmifon chez des malades presentant des symptomes precoces de vieillissement cerebral handicapant leur activite quotidiennne. Etude ouverte pragmatique chez 304 patients. *Vie Medicale* 1990; 2: 335–344.

Lagarde, D., Milhaud, Cl., Anton, G., Jeanneau, A. Modafinil, an original psychostimulant: main properties and approach to the study of its action principles in non human primates. 10th Congress of the European Sleep Research Society, Strasbourg, May 20–25, 1990.

Lagarde, D., Anton, G. Comparative study of stimulant effects of d–Amphetamine Sulfate and Modafinil, an original psychostimulant. Proceedings of the 11th International Congress of Pharmacology; Jul. 1–6, 1990; Amsterdam. Eur.J. Pharmacol., 1990; 184(4):1476.

Lecendreux, M., Gerard, C.L., Bouvard, M.P., Dugas, M. Traitement par modafinil. Effet sur la vigilance, le sommeil, les fonctions cognitives et le comportement chez un enfant prépubère opéré d'un craniopharyngiome. Actes de la Société de Neurophysiologie Clinique de Lange Française. Deuxième réunion trimestrielle: somnolence normale et pathologique. May 30–31, 1991; Montpellier. Neurophysiol Clin. 1991: 21(3) 229–30.

Milhaud CL, Klein M J. Effects de l'Adrafinil sur l'activite nocturne du macaque rhesus (macaca mulatta). *Journal de Pharmacologie* 1985; 16: 372–80.

Moachon, G., Matinier, D., Rambert, F.A., Pessonnier, J., Clenet, M., Duteil, J. Modafinil plasma levels are correlated to locomotor effect in mice. Métabolisme des médicaments. Proceedings de la Séance commune Société française de thérapeutique et de pharmacologie clinique, Association française des pharmacologistes. Besançon, Oct. 19–20, 1989, Fundam. Clin. Pharmacol., 1990, 4:452.

Panckeri, K.A., Schotland, H.M., Pack, A.I., Hendricks, J.C. Modafinil decreases hypersomnolence in the english bulldog, a natural animal model of sleep–disordered breathing. Sleep, 1996 19(8):626–631.

Piérard C, Satabin P, Lagarde D, Barrière B, Guezennec CY, Menu JP, Pérès M.: Effects of a vigilance–enhancing drug, modafinil, on rat brain metabolism: a 2D COSY H–NMR study. *Brain Res* 1995; 251: 251–256.

Pigeau, R., Naitoh, P. The effect of modafinil and amphetamine on core temperature and cognitive performance using complex demodulation during 64 hours of sustained work. In: Neurological limitations of aircraft operations: human performance implications. Proceedings of the Aerospace Medical panel Symposium; Oct. 9–12, 1995, Köln, Germany, AGARD Conference Proceedings, 1996, (579) 39–1–39–11.

Rambert, FA, Pessonnier J, De Sereville J–E, Pointeau, A–M., Duteil J. Profil Psychopharma cologique Originil de l'Adrafinil chez le Souris. *Journal de Pharmacologie* 1986; 17: 37–52. [English Summary].

Rambert FA.; Pessonnier, J.; Duteil, J.: Several aspects of Adrafinil–induced activity in the mouse: involvement of an alpha–adrenergic link. Proceedings of the 14th CINP Congress, Florence Abstract P.177; Jun. 19–24 1984.

Salteu B, Grunberger J, Linzmayer L, Stohr H. Pharmaco–EEG, psychometric and plasma level studies with two novel alpha–adrenergic stimulants CRL 40476 and 40028 (Adrafinil) in elderlies. New Trends In Experimental And Clinical Psychiatry 1986; 11: 5–31.

Shelton J, Nishino S, Vaught J, Dement WC, Mignot E. Comparative effects of modafinil and amphetamine on daytime sleepiness and cataplexy of narcoleptic dogs. Sleep 1995; 18: 817–826.

Simon, P., Chermat, R., & Puech, A.J. (1983). Pharmacological evidence of the stimulation of central alpha–adrenergic receptors. Progress Neuro–Psychopharmacology & Biological Psychiatry, 7, 183–186.

Simon, P., Hemet, C., & Costentin, J. Analysis of stimulant locomotor effects of modafinil in various strains of mice and rats. Fundam Clin. Pharmacol 1996:10:431–435.

Simon, P., Hemet, C., Ramassamy, C., & Costentin, J. (1995). Non–amphetamine mechanism of stimulant locomotor effect of modafinil in mice. European Neuropsychopharmacology, 5, 509–514.

Tanganelli S, Fuxe, K, Ferraro L, Janson, AM, Bianchi C. Inhibitory effects of the psychoactive drug modafinil on –aminobutyric acid outflow from the cerebral cortex of the awake freely moving guinea–pig. *Naunyn–Schmiedeberg's Arch Pharamcol* 1992 ; 345: 461–465.

Touret M, Sallanon–Moulin M, Fages C, Roudier V., Didier–Bazes M, Roussel B, Tardy M, Jouvet M. Effect of modafinil–induced wakefulness on glutamine synthetase regulation in the rat brain. *Mol Brain Res* 1994: 26: 123–128.

Warot, D., Corruble, E., Payan, C., Weil, J.S., Puech, A.J. Subjective effects of modafinil a new central adrenergic stimulant in healthy volunteers: a comparison with amphetamine, caffeine and placebo. Proceedings of the XIXth CINP Congress, Washington, Jun. 27–Jul. 1, 1994. Neuropsychopharmacology. 10, (3S/part2), May 1994.

* cited by examiner

USE OF ADRAFINIL TO TREAT BEHAVIORAL PROBLEMS IN AGED CANINES

FIELD OF THE INVENTION

The present invention relates to novel uses of adrafinil and its metabolites to treat behavioral problems in aged canines.

BACKGROUND OF THE INVENTION

Over the course of aging, the functioning of the central nervous system of dogs, like other mammals, shows a general deterioration. Behaviorally, this deterioration is manifested in a variety of ways, which include decreased exploratory behavior, disturbances in sleep, deficits in housetraining, general restlessness, difficulties in attention, and an overall decrease in motivation. In severe cases, these deficits constitute a canine form of dementia. Behavioral problems in elderly dogs impair the quality of life of the dog, and also decrease the enjoyment of the dog by its master.

The presence of these problems has resulted in the recognition and diagnosis of age-dependent behavioral problems in dogs. The potential importance in sensencent dogs was indicated in a survey by conditions (Chapman, et al., 1990) of 26 aged dogs, greater or equal to 10 years of age. The most common complaints from pet owners were destructive behavior in the house, inappropriate urination or defecation and excessive vocalization. In some cases, pet owners noticed an increase in separation anxiety. In each instance, these dogs were normal when younger. Moreover, these behavioral problems could not be linked to any other medical condition. In fact, one sign of canine senility frequently used by veterinarians is the existence of urinary incontinence, which typically results in the pet owner's decision to euthanize their pet (Mosier, et al., 1988).

These age-dependent behavioral problems also have problematic effects on service dogs. These are highly skilled dogs that are specially trained to carry out a uniquely important function. They include: seeing eye dogs which are trained to help the blind; hearing dogs, which help physically disabled individual who seek increased mobility and independence; special skilled dogs, who are trained on an individual basis based on the person's special needs; and military working dogs, which are trained for a variety of special military functions. The value of these dogs stems in part from the cost of their training. For example, the Lyons foundation in Oakville, Ontario, Canada estimates that the cost to train a single dog is about $20,000. These dogs are typically retired between 7–8 years of age because they become less attentive and slow down.

Age-dependent behavioral problems can be evaluated objectively by neuropsychological tests. The inventors have conducted several studies that were aimed at analyzing learning and memory processes of aged canines. They initially reported that aged dogs performed more poorly than young dogs on a variety of visual base neuropsychological tests (Milgram et al., 1995) and on a spatial memory test (Head et al., 1995). The inventors have subsequently found that aged dogs do particularly poorly on size discrimination learning and reversal task (Head et al., 1998).

More recently, the inventors reported on the basis of an extensive analysis of 54 dogs that level of behavioral functioning of aged dogs could be further broken down into subsets of successful agers, animals with mild impairment, and animals showing severe impairment (Adams et al., 1999). The inventors are able to distinguish two different subcategories of behavioral impairments learning impairment, which is manifested by difficulty in acquiring neuropsychological tasks, and memory impairment, which is manifested by difficulty in performance of tasks that include a delay interval, in which animals must retain a particular set of information. Animals showing severe impairment show both learning deficits and difficulty in retaining information for interval, longer than about 30 seconds.

These changes in behavior and cognition reflect corresponding age-related changes in the central nervous system (CNS). At a molar level, aged dogs show cortical atrophy (Su et al., 1998), and a corresponding increase in the size of the lateral ventricle. Other degenerative changes also occur in the canine brain over the course of aging. At a more molecular level, age dependent changes include distorted soma, loss of dendritic spines, shrinkage of dendritic branches and tortuous apical dendrites (Mervis et a., 1978). DNA damage is another potential indicator of neuronal dysfunction (this is often precursor to apopototic cell death) (Anderson et al., 1997).

Additionally, the aged canine brain develops pathological deposits of beta amyloid protein, which is similar to that seen in the aged humans. The morphology of $A\beta$ deposits in aged dog brain is that of a diffuse subtype. These plaques are thioflavin S negative and therefore probably lack $\beta$-pleated sheet formation (Cummings, et al., 1993). These diffuse deposits appear to contain intact neurons These observations have been made in a variety of breeds (Wegiel, et al., 1996, Yoshino, et al., 1996), although breeds probably differ in their rate and age of onset of $A\beta$ deposition (Bobik, et al., 1994).

The inventors have further shown a direct link between these age-related pathologies and dysfunction in learning and memory. One study of the relationship between cognition and neuropathology examined the extent of $A\beta$ deposition in a group of behaviorally characterized dogs (Cummings et al., 1996). A group of 29 dogs ranging in age from 1.6 to 12–3 years had been tested for reward and object approach learning, visual discrimination and reversal, spatial and object recognition memory. The prefrontal cortex, hippocampus and entorhinal cortex was examined for the extent of $A\beta$ deposition using image analysis techniques. A discriminant analysis of the test scores indicated that two major clusters were present in the behavioral data, one that was termed procedural-type tasks (reward and object approach learning) and the second termed declarative-type tasks (visual discrimination, reversal and memory tasks). The declarative-type tasks, but not the procedural-type tasks were strongly correlated with $A\beta$ deposition in both the prefrontal and entorhinal cortices. In fact, up to 68.97% of the variability in test scores could be accounted for by the amount of $A\beta$ deposition.

In a second study (Head et al., 1998), a more detailed examination was made of 20 beagle dogs ranging in age from 4.5 to 15.3 years of age. These dogs were tested for object and reward approach learning (which the inventors previously established to be independent of $A\beta$ deposition), object discrimination learning using either a preferred or nonpreferred object and size discrimination learning along with long term retention. Based on the nonhuman primate literature, the inventors predicted that some tasks would be sensitive to frontal lobe pathology (reversal learning, object discrimination learning with a nonpreferred object) and that others would be sensitive to temporal lobe function (size discrimination task). Dogs were first classified as being impaired or unimpaired based upon individual error scores obtained from the learning and memory tasks listed previously. An impaired dog was defined as an animal that obtained an error score falling outside the range of error scores obtained by the young dogs. If dogs were separated on this basis then those old dogs that were impaired had significantly higher amounts of Aβ deposition. In addition, dogs with impairments in reversal learning and in object discrimination learning with a nonpreferred object accumulated significantly more Aβ in the prefrontal cortex than unimpaired dogs. This was also true for size discrimination and reward approach learning; impaired dogs had higher amounts of Aβ in the entorhinal cortex (Head, et al., 1998).

In view of the foregoing, there is a need in the art for a treatment for age-related behavioral problems in dogs.

SUMMARY OF THE INVENTION

The inventors have determined that adrafinil is useful in treating behavioral problems in aged canines. Accordingly, the present invention provides a method of treating age related behavioral problems in canines comprising administering an effective amount of adrafinil or an analog, derivative or metabolite of adrafinil to a canine in need thereof.

Age-related behavioral problems that may be treated according to the present invention include learning, urinary incontinence, bladder control, alertness, exploratory behavior, memory and age-related neurological disorders. Overall, treatment with adrafinil and its metabolites improves the overall quality of life for both the canine and its owner.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIGS. 6A and E show computer generated activity pattern printouts. Lines reflect the path followed by the dog in the test room and symbols mark the occurrence of some behaviors [P=urination; S=sniffing; SLEEP=inactivity]. FIG. 6A compares the open field tests of adrafinil to propentofylline. FIG. 6B compares the home cage tests of adrafinil to nicergoline. These patterns illustrate the increase in locomotion produced by adrafinil and the absence of an effect from the other two pharmaceuticals.

DETAILED DESCRIPTION OF THE INVENTION

The present invention relates to a method of treating age related behavioral problems in canines comprising administering and effective amount of adrafinil or an analog, derivative or metabolite of adrafinil to a canine in need thereof.

Adrafinil (CRL 40028) is a crystalline powder, white to rosy beige, with a light sulfurous odor. The chemical name of adrafinil is (diphenylmnethyl)sulfinyl-2 acetohydroxamic acid. Adrafinil has a molecular weight of 289.35 and its empirical formula is $C_{15}H_{15}NSO_3$. It has a melting point of 154° C. with decomposition. It is slightly soluble in water, more so in alcohol and is soluble in methanol.

The term "analog of adrafinil" means any compound that shares structural similarity with adrafinil (although one or more functional groups may be substituted with similar functional groups) and is useful in treating age related behavioral problems in canines.

The term "derivative of adrafinil" means any compound that is derived from adrafinil and is useful in treating age related behavioral problems in canines. This includes a compound where a functional group is chemically derivatized.

Figure 1:
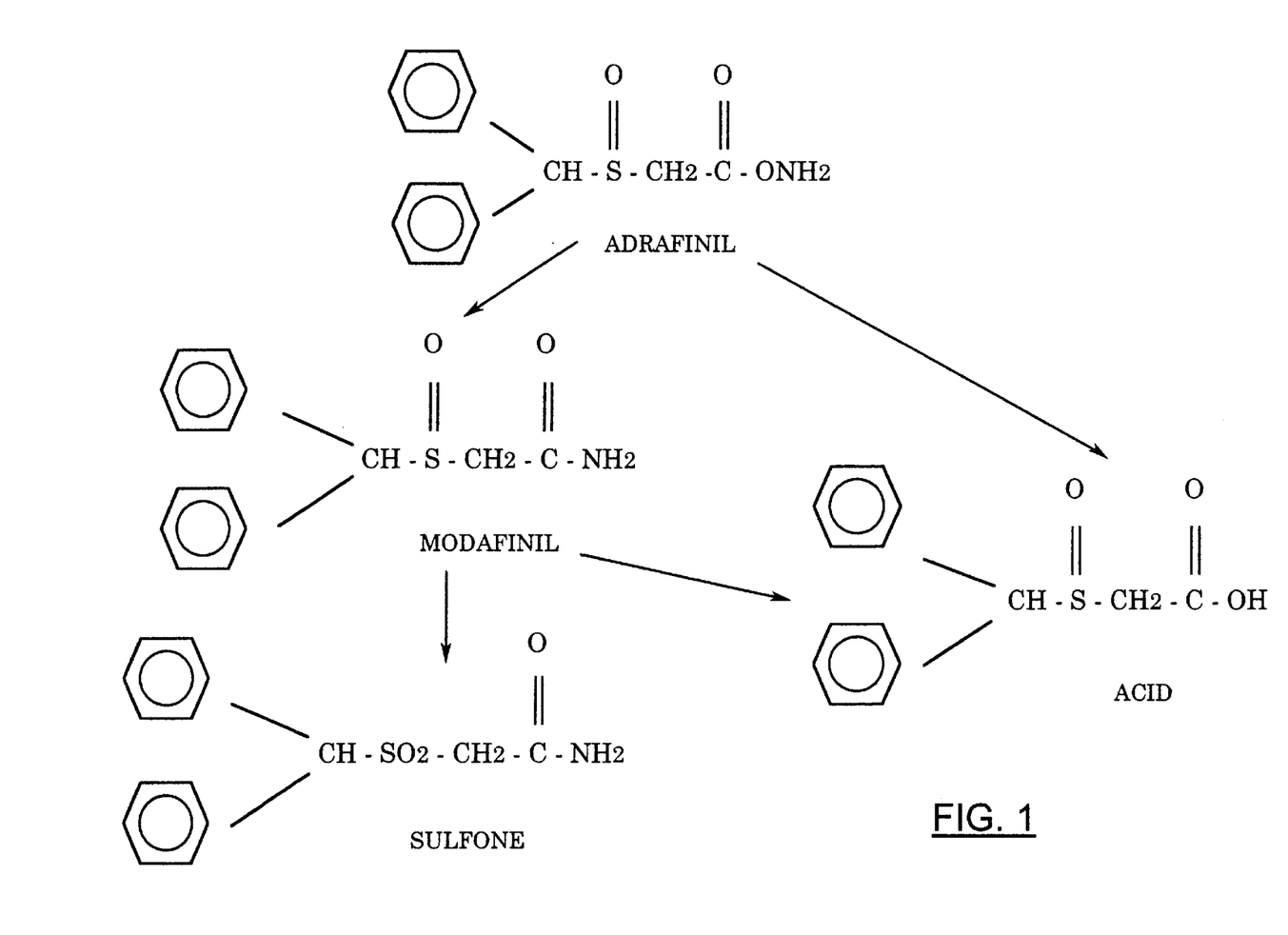
FIG. 1 shows the structure of adrafinil and its metabolites.

The term "metabolite of adrafinil" means any compound that is produced by the metabolism of adrafinil and that is useful in treating age related behavioral problems in canines. The metabolism of adrafinil is shown in FIG. 1. A preferred metabolite of adrafinil is modafinil. The term "adrafinil or an analog, derivative or metabolite of adrafinil" includes pharmaceutically acceptable salts or derivatives of adrafinil or its analogs, derivatives or metabolites.

The term "age related behavioral problem" means any problem that arises from the normal course of aging in a canine. Examples of aged related behavioral problems that may be treated according to the present invention include, but are not limited to, learning, urinary incontinence, bladder control, alertness, exploratory behavior, memory and age-related neurological disorders.

The present inventors have shown in the examples described herein that adrafinil has the following beneficial effects on aged canines.

1. Exploratory Behavior

The inventors have shown that aged canines show increased behavioral activity in a canine open field test at a minimum dose of 20 mg/kg of adrafinil. A much smaller effect is seen on home cage behavioral activity, which suggests that adrafinil enhances exploratory behavior. In one study, adrafinil was compared to propentofylline and nicergoline which have been purported to act as activity-enhancing agents in canines. However, adrafinil was the only one of three pharmaceuticals to produce an increase in activity. Nicergoline and propentofylline had no effect.

2. Bladder Control

The inventors have also shown that adrafinil at a dose of 40 mg/kg decreases frequency of urination in aged dogs in a canine open field test.

3. Learning/Memory

The inventors have further shown that adrafinil can counteract, or reverse age-dependent deterioration in mental functioning, particularly discrimination learning and an acquisition of an object recognition task.

In one study, the inventors demonstrated that adrafinil improves performance on discrimination learning tasks in aged beagle dogs. Three of four behaviorally impaired dogs showed improved performance on an object recognition memory task after treatment with adrafinil. The fourth animal did not show the expected increase in open field activity.

One severely impaired dog showed more rapid responding after treatment with adrafinil, when tested on a spatial memory task. This increase in responding suggests increased central nervous system processing speed.

On discrimination learning task, adrafinil reduced the frequency of response failure in one dog, as presented in example 3. Frequency of response failures was also reduced in one other dog that was tested on a spatial memory task.

The improvement in learning and memory caused by adrafinil can not only be useful for dogs that are pets but is also very useful for service dogs. Adrafinil can prolong the productive lifespan of service dogs by improving their attention and working memory capacity.

4. Age-Related Neurological Disorders

Maintenance of aged canines on adrafinil will retard the development of both age dependent neuropathology and neurological disorders.

For all of the above indications, adrafinil or its metabolite is administered in an amount effective, at dosages and for periods of time necessary to achieve the desired result (referred to herein as an "effective amount"). Preferably, the adrafinil or its metabolite is administered in an amount from about 10 to about 50 mg/kg, preferably from greater than 10 mg/kg to about 50 mg/kg and more preferably from about 20 to about 40 mg/kg. For the treatment of urinary dysfunction, a dose of about 40 to about 50 mg/kg is preferred.

The adrafinil and its metabolites is preferably administered orally by way of a tablet, capsule or solution. The adrafinil can also be administered through any other suitable route such as parenterally, intravenously, subcutaneously, intramuscularly, transdermally or rectally.

Figure 2:
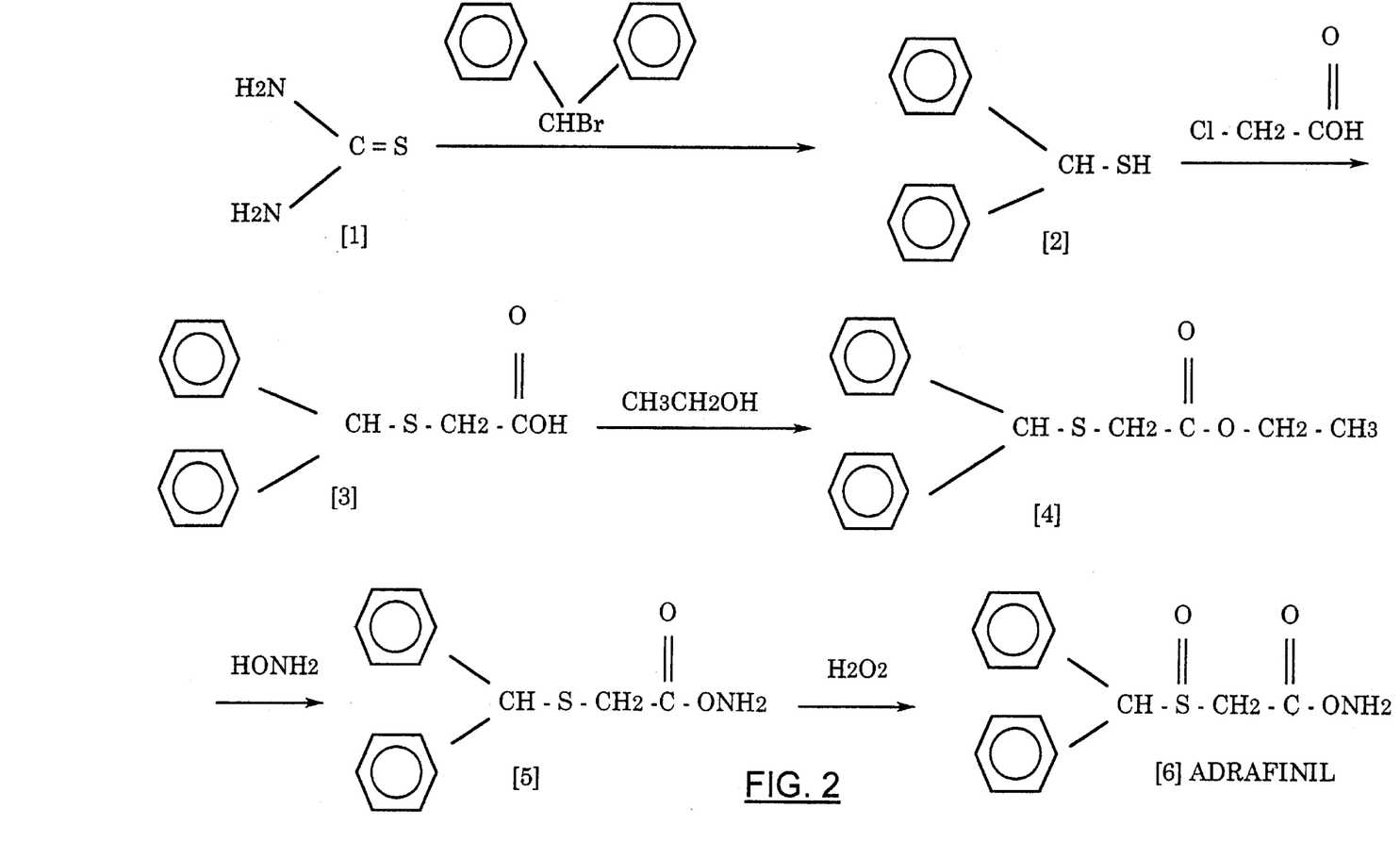
FIG. 2 shows the chemical synthesis of adrafinil.

The adrafinil can be obtained from commercial sources or can be synthesized according to the reaction scheme shown in FIG. 2. Once synthesized, the adrafinil can be formulated into a pharmaceutical composition suitable for administration to canines. The composition can be prepared by per se known methods for the preparation of pharmaceutically acceptable compositions which can be administered to dogs, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., U.S.A. 1985) On this basis, the compositions include, albeit not exclusively, solutions of the substances in association with one or more pharmaceutically acceptable vehicles or diluents, and contained in buffered solutions with a suitable pH and iso-osmotic with the physiological fluids.

EXAMPLES

Example 1

Effects on Exploratory Behavior

The effect of adrafinil on open field activity of aged canines was examined in three separate studies The first study was intended to provide dose-response and time-course data. The second study looked at the effect of repeated administration and obtained further dose-response findings. The third study compared adrafinil to two other pharmaceuticals and introduced a home-cage activity test.

1.1 Dose Response Analysis of Effects of Adrafinil on Canine Spontaneous Behavior This and all subsequent studies used an open field activity test as described by Head and Milgram (1992). Dogs are placed in an empty room and its behavior is observed and recorded using a dedicated computer program. The floor is marked into squares to facilitate tracing the dogs' movement pattern. The behaviors recorded include locomotion, sniffing, urination, inactivity, grooming, rearing, vocalizing and jumping. Total distance is recorded for locomotion, total time for inactivity and grooming, and frequency of occurrence of the remaining behaviors.

The subjects used in this study were 9 Beagle dogs of both sexes obtained from Harlan Sprague Dawley Breeding Farms. In this, as well as all other studies, the dogs were middle aged, or old (7 years or more). In this study each dog was tested 3 times on adrafinil and 3 times on a placebo control. Dogs were assigned to one of three dose levels (10, 30 or 50 mg/kg) and spontaneous behavior measurements were then obtained at one of three time points, 2, 4 or 10 hours after oral administration of the treatment. The dogs only received the drug on the day of testing and were tested at corresponding times on a placebo control. The order of treatments and intervals was randomly determined. Open field tests took place every fourth day.

Figure 3A:
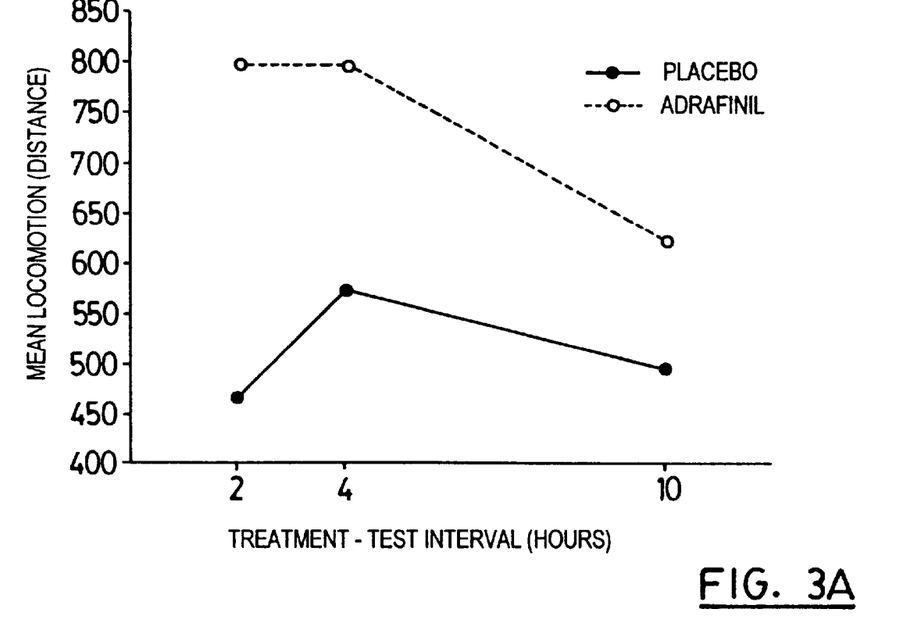
FIGS. 3A and B are graphs showing locomotion increase under adrafinil treatment. Graph A shows that adrafinil increased locomotion at all test intervals. Graph B indicates that the increase in locomotion is dose dependent.
Figure 3B:
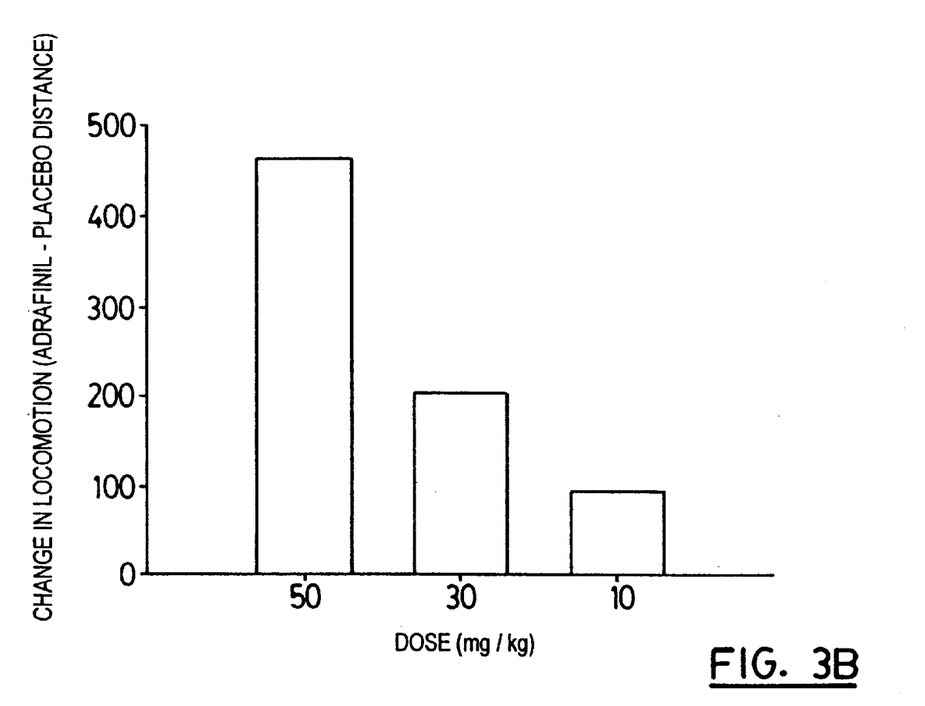

This study revealed that locomotor activity is significantly increased in aced dogs when treated with adrafinil (p=0.0018). The results of this study are shown in FIG. 3. The increase in activity was dose (p=0.0353) and time (p=0.0635) dependent. Higher doses produced greater increases and longer drug-test intervals resulted in lower levels of activity. It was noted that the response to adrafinil varied among the individual dogs. One dog did not show an increase in activity in response to the highest dose level. This was the only dog to show a fearful response when placed in the test room and it spent the entire session in one place.

Urination frequency was significantly decreased (p=0.0405) but only at the highest dose level. Stereotyped behavior was not observed with adrafinil treatment. Each dog displayed a unique pattern of behavior and this was not affected by drug treatment.

This study, therefore, showed that adrafinil can increase open field activity and that the effect is dose and time dependent. The second study looked at this relationship in more detail and examined the effects of chronic treatment (Siwak et al., submitted).

1.2 Effect of Repeated Administration

A crossover design was used with 32 beagle dogs. Dogs were treated with either adrafinil or placebo for 14 consecutive days. Following an eight-day washout period the treatment was switched and administered daily for 14 days. Thus, half of the dogs started with adrafinil and ended with placebo, while the other half started with the placebo and ended with adrafinil. Four different dose levels were used, 10, 20, 30 and 40 mg/kg. Eight dogs were assigned to each dose level.

Figure 4A:
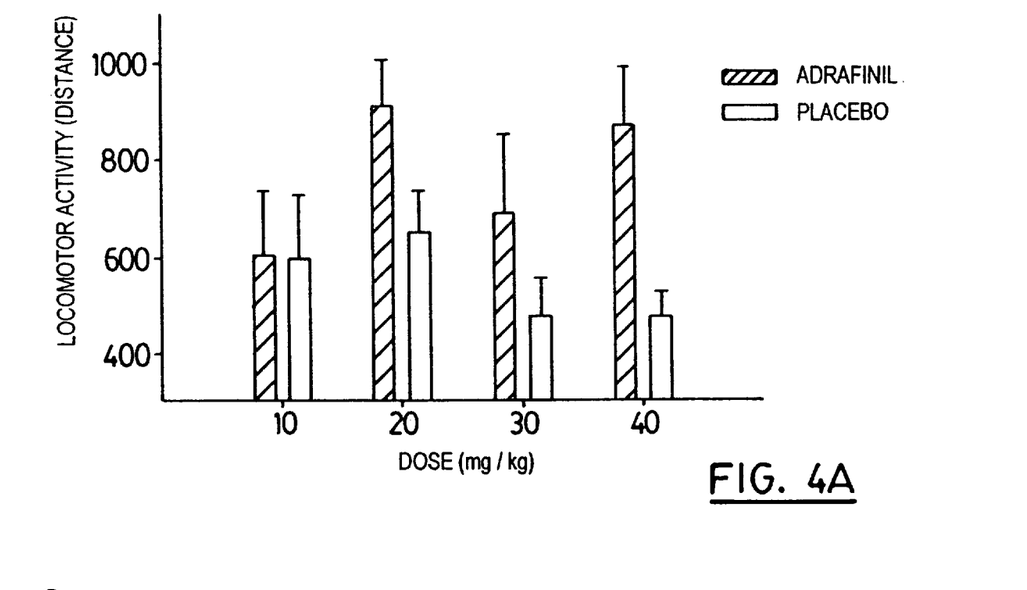
FIGS. 4A and B are graphs showing dose-response relationship of adrafinil treatment and locomotor activity. Graph A shows that a reliable increase in locomotion is observed between doses of 20–40 mg/kg. Graph B illustrates the dose dependency of the effect. Error bars represent standard errors.
Figure 4B:
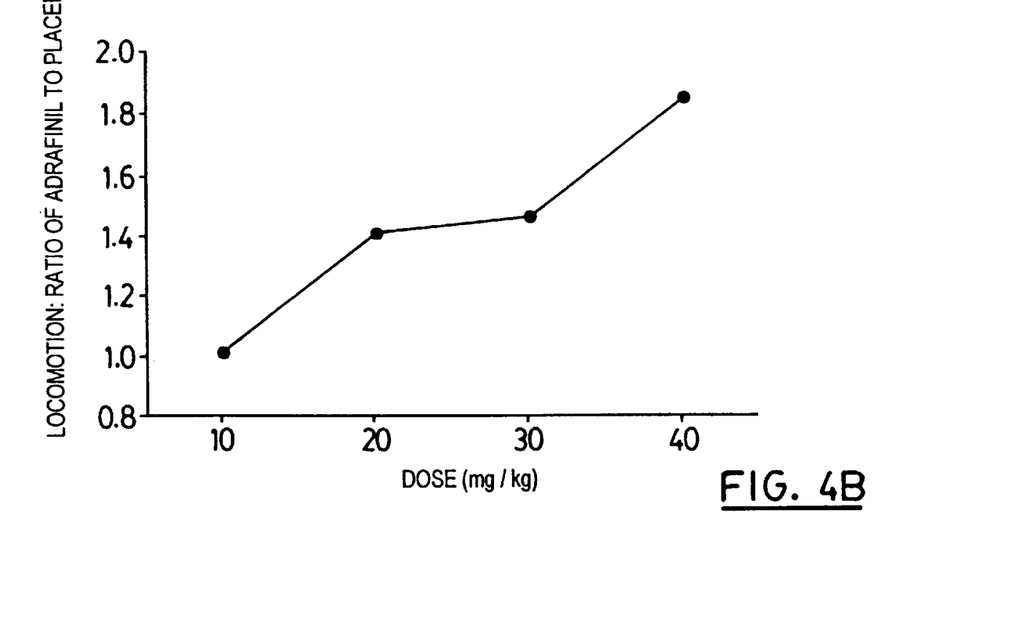

As illustrated in FIG. 4, adrafinil reliably increased locomotor activity at doses between 20 and 40 mg/kg with the effect being dose-dependent. Stereotyped behavior was generally not observed but individual differences in the response to adrafinil treatment were observed. Some animals showed either no response or decreased locomotion after treatment with adrafinil.

Other behaviors were also affected by adrafinil. Urination frequency in particular was decreased but only at the highest dose level. Adrafinil did not produce a consistent increase in any other behavior. Sniffing showed a transient increase but this had disappeared by the second test session. Grooming, vocalization, rearing and jumping showed no consistent effects.

The inventors also found an unexpected effect of test order. The group treated with the placebo first showed smaller increases in locomotion under adrafinil than the adrafinil-placebo group. This result suggested that the effectiveness of adrafinil is situation dependent. The placebo-adrafinil group had had six tests in the open field arena prior to treatment with adrafinil. This made the test environment familiar to the dogs and likely reduced the effectiveness of adrafinil in increasing activity. The activity increase induced by amphetamine has also been shown to be influenced by environmental variables (Raskin, 1983). She found that amphetamine-treated animals are more active in a novel environment than in a familiar one. Her study also showed that directed activity is increased in young rats treated with amphetamine when an anesthetized conspecific is placed in the cage. Undirected activity does not differ significantly.

Figure 5A:
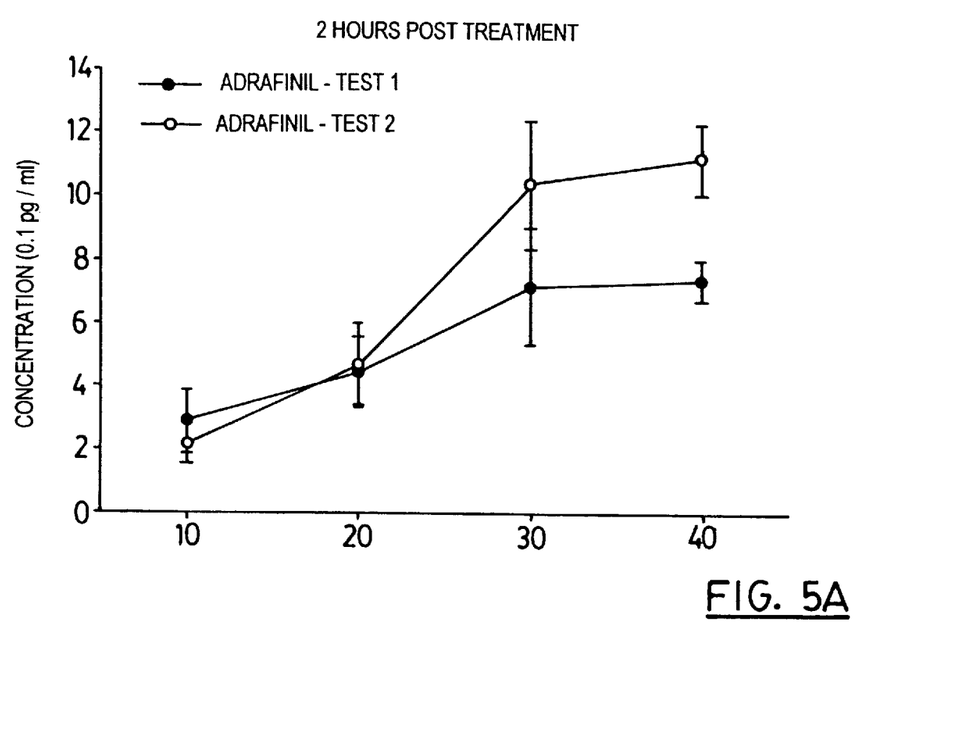
FIGS. 5A and B are graphs showing serum levels of adrafinil showed a dose-dependent increase at 2 hours after dosing. At 10 hours, levels of adrafinil were lower in the high dose group (40 mg/kg) than the low dose group (10 mg/kg).
Figure 5B:
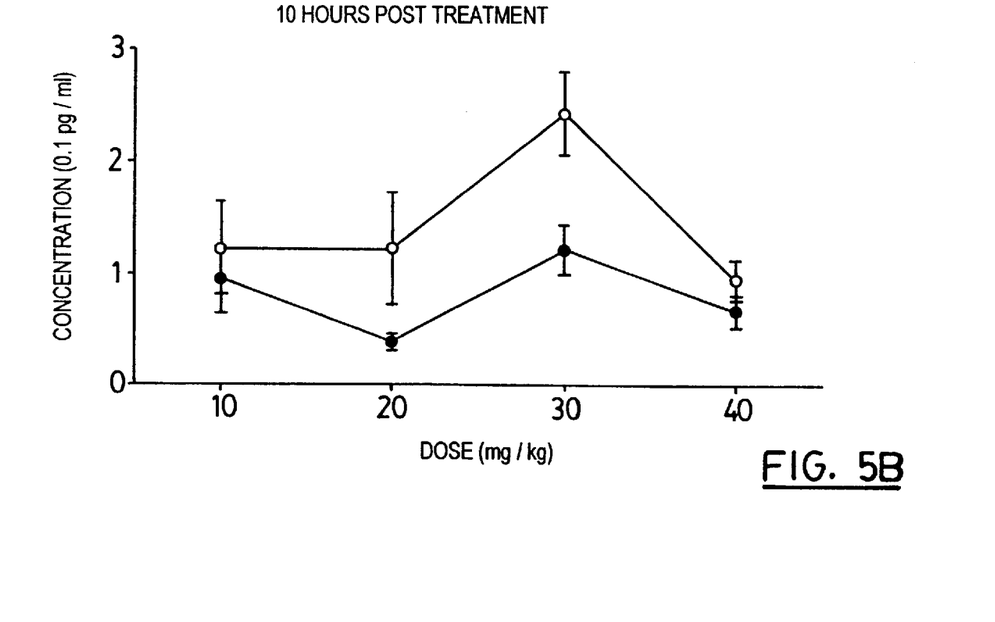

In the dog, adrafinil is metabolized to an active metabolite, modafinil, and an inactive acid metabolite. To determine the relationship between the activity increase and each metabolite, we used high performance liquid chromatography to measure serum levels of adrafinil, modafinil and the acid form at 2 and 10 hours following treatment. Adrafinil showed a dose dependent increase at 2 hours after dosing (FIG. 5). At 10 hours, however; serum levels of adrafinil in the high dose (40 mg/kg) group were actually lower than the low dose (10 mg/kg) group, suggesting adrafinil itself may affect metabolism and elimination processes.

The inventors found differences between responders and non-responders in serum concentrations of adrafinil. The dogs that showed activity increases had higher levels of adrafinil at 2 hours post treatment than non-responders and lower levels at 10 hours. These observations suggest that differences in the rate of metabolism may account for differences in animals' behavioral responses.

1.3 Comparison of the Effects of Adrafinil, Propentofylline, and Nicergoline on Home Cage and Open Field Activity in Aged Beagles Our third study compared adrafinil to two other pharmaceuticals purported to serve as activity-enhancing agents for canines, propentofylline and nicergoline. In addition to the open field test, we developed a home cage observation test to evaluate the effectiveness of the drugs in enhancing activity in a familiar environment.

Propentofylline is a xantine derivative that inhibits adenosine uptake (Fredholm and Lindström, 1986). Propentofylline is commercially available in the United Kingdom as a canine pharmaceutical called Vivitonin that is claimed to improve activity deficits in aged dogs. It is currently undergoing clinical trials for use with human Alzheimer's patients. Nicergoline is an ergoline derivative commercially available in Europe as Fitergol. It is claimed to improve the quality of life in elderly dogs.

Figure 6A:
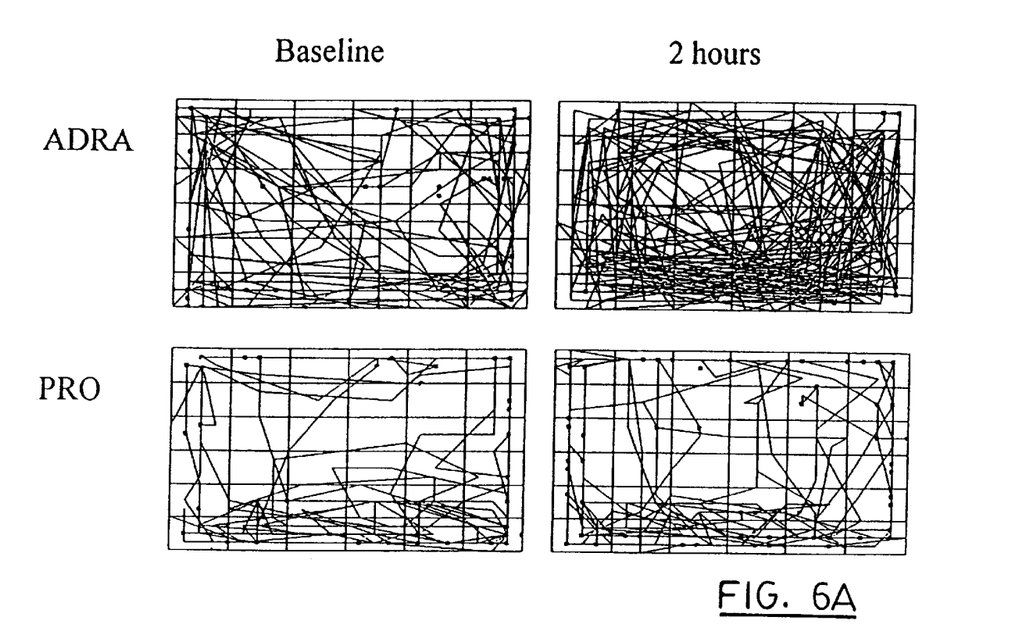
Figure 6B:
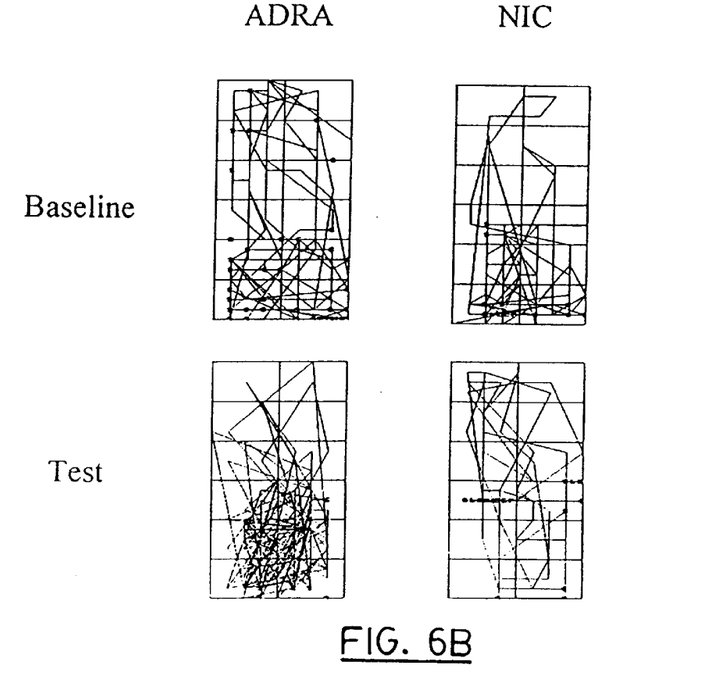

Thirty-six beagle dogs were treated with one of the three pharmaceuticals for 33 consecutive days. Adrafinil was the only drug to produce an increase in activity (FIG. 6). In the open field adrafinil produced a dramatic increase in locomotor activity that persisted for the duration of the study. Adrafinil also produced an increase in activity in the home cage but the effect was much smaller. The home cage is a highly familiar environment whereas the open field is novel. Activity levels in the home cage are lower than in an open field yet adrafinil caused an increase in activity in both environments. This suggests that adrafinil is more effective in a novel environment but can still cause an increase in activity in a familiar one. This supports the findings in our previous study where dogs treated with adrafinil after having had placebo tests showed a smaller increase in activity.

Conclusions

The above studies demonstrate that adrafinil causes increased locomotor activity in dogs, and that the effectiveness is not diminished after over a month of daily treatment. These effects are dose dependent, with a dose of about 20 mg/kg being the minimum necessary for producing a reliable effect. The activity promoting effects of adrafinil in dogs are also long lasting, and can persist for up to 10 hours. Individual differences exist in the response of aged dogs to adrafinil treatment. These differences may be related to individual differences in metabolism. The effectiveness of adrafinil also varied as a function of experience in the testing environment. Larger effects are observed in unfamiliar environments but activity increases are still observed in highly familiar ones.

Example 2

Effects of Adrafinil on Learning and Memory

The following series of experiments were conducted to examine the effects of adrafinil on learning and memory of aged beagle dogs. The first study examined discrimination learning. The inventors also evaluated the effect of adrafinil on performance motivation in a group of unreliable responders. A final study looked at the effect on spatial memory in a demented dog and on object recognition learning in a group of behaviorally impaired dogs.

2.1 Enhancement of Discrimination Learning

Eight beagle dogs were trained on two discrimination learning tasks, size and intensity (Milgram et al., sub). The dogs were tested on one task under a 20 mg/kg, dose of adrafinil and on the second task under a placebo control. Both task order and treatment order were counterbalanced so that half of the dogs were tested first under adrafinil, and half of these were tested on the size discrimination task, while the other half were tested on the intensity discrimination task. The number of trials and the number of errors to reach criterion were analyzed. The results of this study are summarized in FIG. 7, they show that adrafinil improves the performance of dogs relative to their performance under a placebo in the acquisition of a discrimination learning task.

2.2 Improved Performance Motivation

Figure 7:
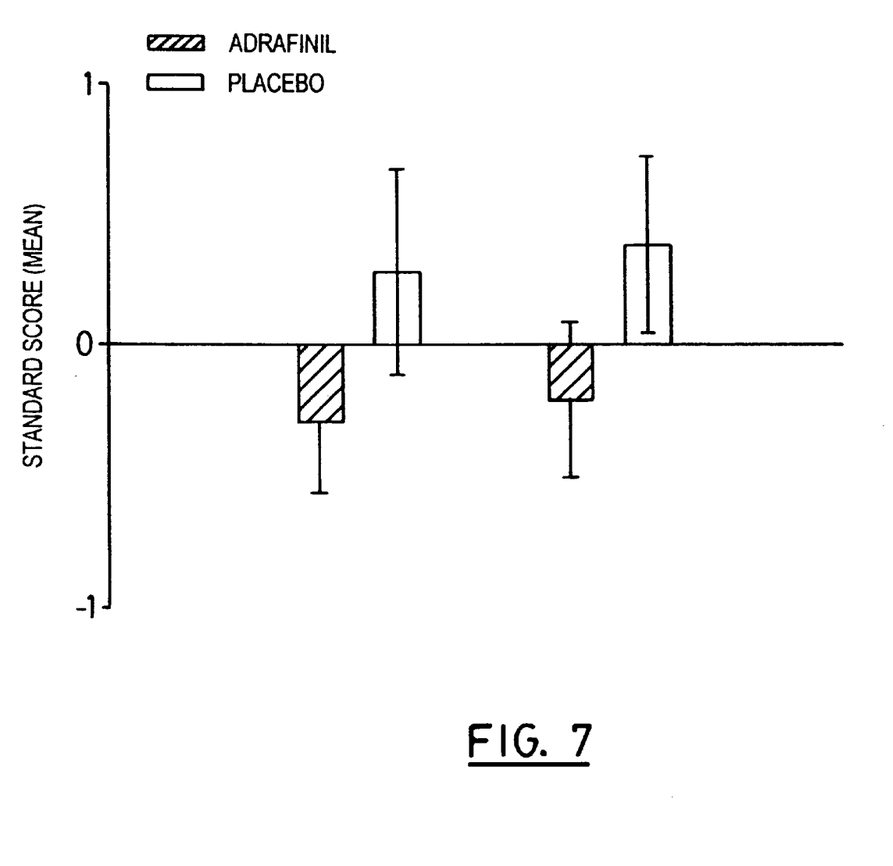
FIG. 7 is a graph showing that adrafinil improves the performance of dogs relative to placebo on discrimination learning tasks. The standard score was calculated to eliminate differences in task difficulty. Error bars reflect standard errors.
Figure 8A:
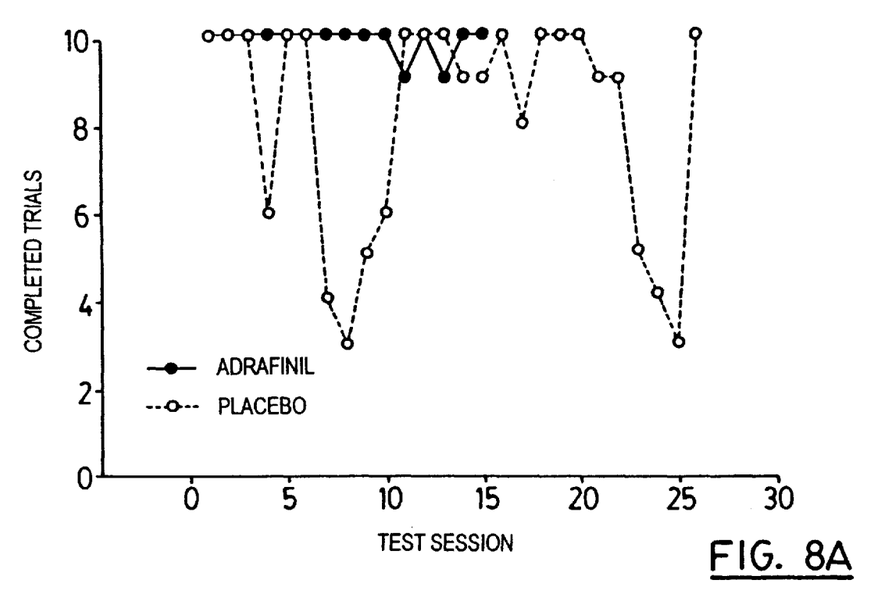
FIGS. 8A and B are graphs showing adrafinil produced a marked improvement in response motivation. Graph A illustrates the number of trials per session to which one dog responded during the acquisition of discrimination learning tasks. Graph B plots the mean number of responses per session to which another dog responded during a spatial memory task. Error bars indicate standard errors of the mean.
Figure 8B:
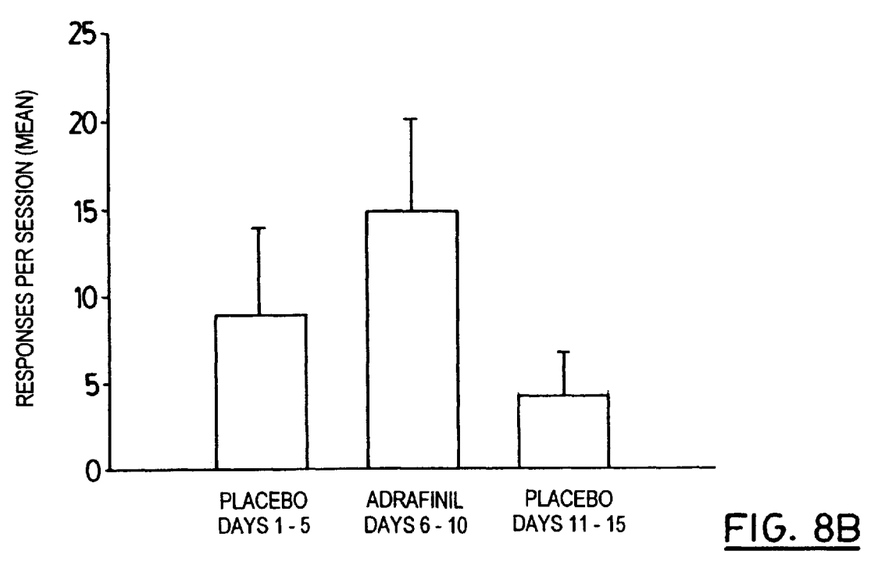

On discrimination learning as well as other tests of learning and memory, the dogs' motivation to respond comes at least in part from their desire to obtain food reward. Over prolonged testing, however, there were several instances of animals that either stop responding, or become inconsistent responders. The term performance motivation is used to refer to whatever factors account for consistency in behavioral responding. The inventors have some evidence to suggest that adrafinil can increase the animals performance motivation to respond on behavioral tasks. One of the subjects used in the discrimination learning study discussed above showed marked response failures during a pretraining discrimination task and the discrimination task under placebo. When this dog was administered adrafinil she showed a marked improvement in motivation to respond as illustrated in FIG. 7A.

The inventors subsequently looked at the effects of adrafinil on performance motivation on a spatial memory task with two other dogs that have consistently failed to respond during testing. The spatial memory task requires two presentations of the objects, a sample presentation and a choice presentation. This requires more responses from the dog than the discrimination task. The dogs were tested under placebo for a 5-day period, adrafinil for another 5-day period followed by a second period of 5 days under placebo. One dog showed improvements in performance motivation under adrafinil. The number of responses under adrafinil was greater than the placebo condition (FIG. 6B). The second dog did not improve under adrafinil. Administration of adrafinil was short-term for these two dogs.

Adrafinil can improve performance motivation. However, its effectiveness can be variable. Further research should be conducted in this area using a repeated administration protocol as was used in the first discrimination study described.

2.3 Object Recognition Learning

A group of behaviorally impaired dogs was used to determine whether adrafinil could assist in the acquisition of an object recognition learning task (see Callahan et al., sub). Four aged dogs were given 80 sessions to learn a delayed-non-matching to sample task and were unsuccessful. (Normal aged dogs learn this task in less than 40 sessions.) After treatment with adrafinil, three of the four aged dogs showed improved performance on the object recognition memory task.

2.4 Increased High Frequency Cortical EEG in Canines

The inventors have also examined the effects of oral administration of adrafinil on resting EEG activity. EEG provides a physiological measure of the effectiveness of adrafinil on activity in the central nervous system, the cortex in particular. Low frequency EEG is associated with intellectual decline. Three beagle dogs (over 10 years of age) were implanted with stainless steel electrodes in the parietal lobe. Baseline EEG recordings were taken for 8 days prior to the start of treatment over 5 hour periods. Two dogs were given 20 mg/kg of adrafinil for 8 consecutive days and resting EEG was taken for 5-hour periods following drug administration. The third dog received 10, 20 and 40 mg/kg of adrafinil. Each dose was administered for 3 consecutive days with a 4-day washout period between doses.

A computer-assisted power spectrum analysis indicated that adrafinil administration induced an arousal-type state for all three dogs. There was an increase in alpha and beta activity and a decrease in delta and theta activity. No differences were observed between the different doses. The activating effects of adrafinil remained for 4 hours following drug administration. Saletu et al. (1986) obtained similar results in aged humans who were given oral doses of 200–900 mg of adrafinil prior to EEG testing. They found that adrafinil caused a decrease in slow waves (in the delta and theta frequency bands) and in the very fast beta activity. In contrast, alpha activity increased and there was a trend towards an increase in slow beta activity.

Differences between the animals were correlated with the frequency composition of the baseline EEG. Dogs that had an initial resting EEG composed predominantly of lower frequencies (delta and theta) showed a greater increase in alpha and beta activity than dogs that had a high alpha and beta activity prior to drug treatment. These differences in EEG composition may be partly due to age differences of the dogs. As a dog ages, we typically see an increase in the low frequencies and a decrease in the higher frequencies, especially alpha activity. This was also the case in the baseline EEG activity of the old dogs that were tested. The activating effects of adrafinil appeared to counter-act this effect.

Example 3

Introduction

The purpose of the present study was to obtain dose-response findings on the effect of modafinil on spontaneous behavior of aged beagle dogs.

Methods

Subjects included in this report were 14 beagle dogs. Prior to the start of the study, each of the dogs were given two 10 minute open-field tests, using testing procedures described previously (Head and Milgram, 1995). For each animal, the total amount of locomotor activity during each of the baseline tests was calculated, and the mean score was used in allocating the dogs to the experimental groups. A counterbalanced procedure was used to assure that all groups had an equal of high active and low active animals. A total of four animals were in both the 10 and 30 mg/kg dose groups. Three animals were in each of the other two groups.

The procedures used have been described previously (Head and Milgram). The activity tests took place in a 3.66×3.66 m test room containing a sink and cupboards. There are two large Plexiglas windows and two doors in the walls of the room. All windows were covered with black plastic excluding a small area for observing and videotaping the dogs.

The test sessions were 10 minutes in duration. The dog was placed just inside one doorway of the room and was observed by an experimenter who recorded the animal's behavior with a video camera. All observations and data analysis was done blindly. The resulting videotape was analyzed using a dedicated program that revealed total amount of locomotor activity, directed sniffing, urination, inactivity, grooming, jumping, rearing and vocalization. For locomotor activity, grooming, and inactivity, the program provided a measure of total distance or time. A frequency of occurrence measure was used in characterizing the other behaviors.

All treatments were administered two hours prior to the open field test session.

Results

Figure 9:
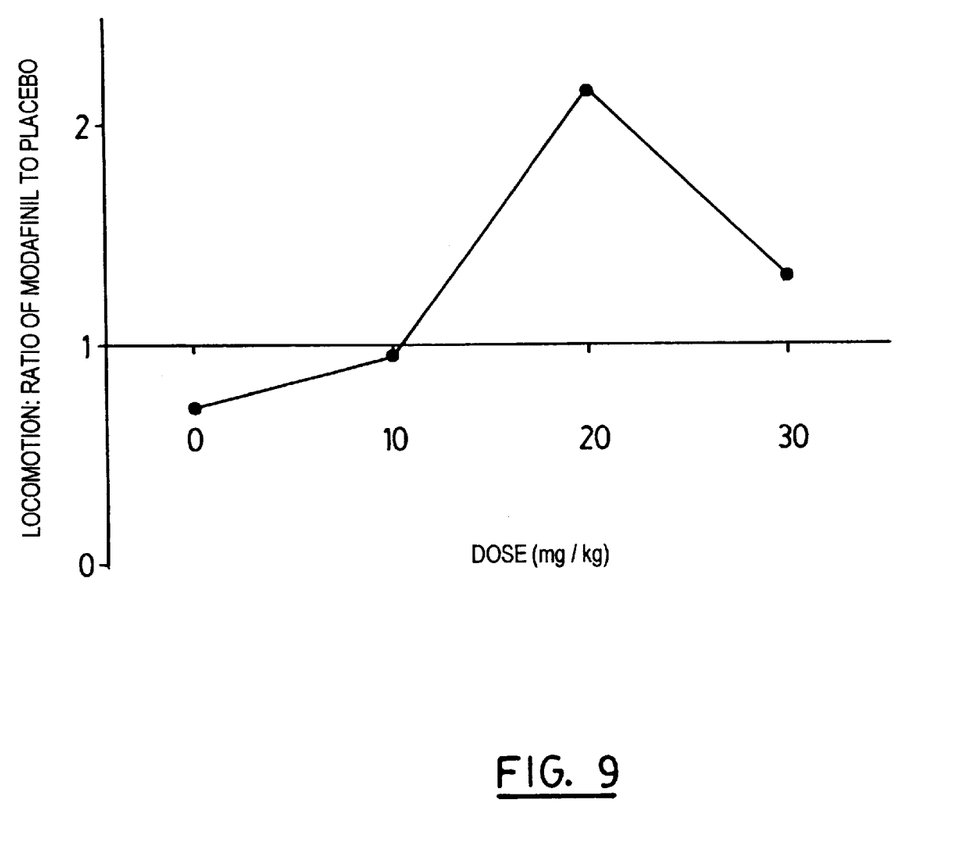
FIG. 9, is a graph illustrating the ratio of locomotor activity under modafinil to locomotor activity under placebo control. The graph shows that modafinil markedly increased locomotion at dose levels of 20 and 30 mg/kg.

The results are summarized in FIG. 9. Modafinil markedly increased locomotion at dose levels of 20 and 30 mg/kg. Mean locomotion score was slightly lower than baseline for the placebo control group and for the group administered a dose of 10 mg/kg.

We also recorded grooming, sniffing, rearing, and vocalization. None of these measures showed any clear effect.

Discussion

The results of this study indicate that modafinil produces an increase in locomotor activity in aged dogs, and that the increase is dose dependent. In the present study the minimum dose required to see an effect was 20 mg/kg, as can be seen from. FIG. 9 which shows the ratio of locomotor activity under modafinil to locomotor activity under placebo control. The figure illustrates that animals treated with a dose of 20 mg/kg showed a level of locomotor activity under modofinil that was more than twice that under baseline.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

DETAILED REFERENCES

Anderson, A. J. Ruehl, W. W., Fleischmann, L. K., Stenstrom, K., Entriken, T. L. and Cummings B. J., (1997). DNA damage is correlated with Abeta deposition and unrelated to cytoskeletal neuropathology in the canine model of Alzheimer's disease. Society for Neuroscience Abstracts.

Boyer P. Age et performance cognitives, plaintes mnesiques et attentionnelles au quotidien. Synapse n spécial "Vers une medecine des comporterments", 1994: pp 1–4.

Boyer P, Weil J S, Lubin S, Von Frenckell R. Inhibition de l'action et handicap idéomoteur. Résultats d'une étude controlée Adrafinil (Olmifon) versus placebo. Synapse 1991: 81.

Cabib S, Castellano C. Impairments produced by amphetamine and stress on memory storage are reduced following a chronic stressful experience. *Psychopharmacology* (Berl) 1997 January; 129(2):161–7.

Callahan H M, Head E, Cotman C W, Milgram N W. Development of a protocol for studying object recognition memory in the dog. In submission.

Chapman, B. L., and Voith, W. L. (1990). Behavioral problems in old dogs: 26 cases (1984–1987). JACMA 196 (6):944–946.

Cummings, B. J., Head, E., Ruehl, W., Milgram, N. W., & Cotman, C. W. The canine as an animal model of human aging and dementia. (1996). Neurobiology of Aging, 17, 259–268.

Defrance D, Raharison S, Hervé M A, Fondaraï J Bétrancourt J C, and Lubin S. Malade ages institutionnalises et Olmifon (adrafinil): determination d'un profil de "repondeurs" a l'occasion d'un "effect centre" lors d'un essai controle versus placebo. *Actualité Médicales Internationales Psychiatrie* 1991; 8: 1815–1823.

Delini-Stula A, Hunn C. Effects of single and repeated treatment with antidepressants on the apomorphine-induced yawning in the rat: the implication of –1 adrenergic mechanisms in the D-2 receptor function. *Psychopharmacol* 1990; 101: 62–66.

Dewailly, P.; Durocher, A. M.; Durot, A.; Bukowski, J. V.; Frigard, B.; Herbin, H.; Lemaire, P.; Kohler, F.; Betrancourt, J. C. Lubin, S.: Adrafinil et ralentissement du sujet age institutionnalise: de la significativite statistique a la pertinence clinique (resultat d'une etude multicentrique en double aveugle versus placebo). *Actualites Medicales Internationales Psychiatrie* 1989; 6: 1–8.

Duteil J, Rambert F A, Pessonnier J, Gombert R, Assous E. A possible alpha-adrenergic mechanism of drug (CRL 40028)-induced hyperactivity. *Eur J Pharmacol* 1979; 59:121–123.

Ferraro L, Tanganelli S, O'Connor W T, Antonelli T, Rambert F, Fuxe E. The vigilance promoting drug modafinil increases dopamine release in the rat nucleus accumbens via the involvement of a local GABAergic mechanism. *Eur J Pharmacol*, 1996; 306: 33–39.

Fontan, Fondaraï J, Micas M, Albarède J-L.: Interet de la psychometrie informatisee dans l'appreciation de l'activite d'Olmifon (adrafinil) on alertness and cognitive performance in elderly retirement home patients. *Psychologie Medicale* l1990; 22: 253–267.

Fredholm B B, Lindström F. The xanthine derivative 1-(5-oxohexyl)-3-methyl-7-propyl xanthine (HWA) enhances the actions of adenosine. Acta Pharmac Toxic 1986 58: 187–192.

Hascoët M, Bourin M. A new approach to the light/dark test procedure in mice. *Pharmacol Biochem Behav* 1998; 60: 645–653.

Head, E. & Milgram, N. W. (1992) Changes in spontaneous behavior in the dog following oral administration of L-deprenyl. Pharmacology, Biochemistry & Behavior, 43, 749–757.

Head, E., Callahan, H., Cummings, B. J., Muggenberg, B. A., Cotman, C. W., & Milgram, N. W. (1998). Visual-discrimination learning ability and β-amyloid accumulation in the dog. Neurobiology of Aging, 19 (5) 415–425).

Head, E.; Milgram, N. W.: Changes in Spontaneous Behaviour in the Dog Following Oral Administration of L-Deprenyl. Pharmacol. Biochem. Behav. 43: 749–757; 1992.

Head E, Callahan H, Cummings B, Cotman C W, Ruehl W W, Muggenburg B A, Milgram N W. Open Field Activity and Human Interaction as a Function of Age and Breed in Dogs. *Physiology & Behavior* 1997 62(5): 963–971.

Ishikawa K, Saito S. Differences in the effects of post-trial chloropromazine, reserpine, and amphetamine on discrimination learning in rats. *Psychopharmacology* (Berl) 1976 July 9;48(1):45–51.

Israel L, Fondarai J, Lubin S, Salin B, Hugono, R. L'Adrafinil (Olmifon) et patients âgés ambulatoires. Efficacité, versus placebo, de l'Adrafinil sur l'éveil dans les activités de la vie quotidienne. *Psychologie Médicale* 1989; 21: 1235–1255.

Jouvet M. Une nouvelle famille de medicaments pour ameliorer l'eveil: les eugregoriques. Journées d'etude sur le vieillissement, organisees par l'orphem, 1987; 25 . 26.

Kohler F, Lubin, S. Etude en medecine generale de l'interet therapeutique d'Olmifon chez des malades presentant des symptomes precoces de vieillissement cerebral handicapant leur activite quoitidienne. Etude ouverte pragmatique chez 304 patients. *Vie Medicale* 1990; 2: 335–344.

Milhaud C L, Klein M J. Effects de l'Adrafinil sur l'activate nocturne du macaque rhesus (macaca mulatta). *Journal de Pharmacologie* 1985; 16: 372–80.

Milgram N W, Siwak C, Gruet P, Woehrle F, Callahan H. Oral administration of adrafinil improves discrimination learning in aged beagle dogs. In submission.

Oscos A, Martinez J L Jr, McGaugh J L. Effects of post-training d-amphetamine on acquisition of an appetitive autoshaped lever press response in rats. *Psychopharmacology* (Berl) 1988;95(1):132–4.

Piérard C, Satabin P, Lagarde D, Barrière B, Guezennec C Y, Menu J P, Pérès M. Effects of a vigilance-enhancing drug, modafinil, on rat brain metabolism: a 2D COSY H-NMR study. *Brain Res* 1995; 251: 251–256.

Rambert, F A, Pessonnier J, De Sereville J-E, Pointeau, A-M, Duteil J. Profil Psychopharmacologique Originil de l'Adrafinil chez le Souris. *Journal de Pharmacologie* 1986; 17: 37–52.

Raskin L A. The Influence of Environmental Variables on Amphetamine-Induced Activity in the Preweanling Rat. Pharmacology Biochemistry & Behavior 1983; 19:187–191.

Salinas J A, Williams C L, McGaugh J L. Peripheral post-training administration of 4-OH amphetamine enhances retention of a reduction in reward magnitude. *Neurobiol Learn Mem* 1996 March; 65(2)b 192–5.

Salteu B, Grunberger J, Linzmayer L, Stohr H. Pharmaco-EEG, psychometric and plasma level studies with two novel alpha-adrenergic stimulants CRL 40476 and 40028 (Adrafinil) in elderlies. *New Trends In Experimental And Clinical Psychiatry* 1986; 11: 5–31.

Siwak C T, Gruet P, Woehrle F, Muggenburg, B, Murphey, H L, Milgram, N W. Comparison of the effects of adrafinil, propentofylline and nicergoline on spontaneous behavior of aged dogs. In preparation.

Siwak C T, Gruet P, Woehrle F, Schneider M, Muggenburg B A, Murphey H, Callahan H, Milgram N W. Behavioral Activating Effects of Adrafinil in Aged Canines. In submission.

Tanganelli S, Fuxe, K, Ferraro L, Janson, A M, Bianchi C. Inhibitory effects of the psychoactive drug modafinil on -aminobutyric acid outflow from the cerebral cortex of the awake freely moving guinea-pig. *Naunyn-Schmiedeberg's Arch Pharmacol* 1992; 345: 461–465.

Touret M, Sallanon-Moulin M, Fages C, Roudier V., Didier-Bazes M, Roussel B, Tardy M, Jouvet M. Effect of modafinil-induced wakefulness on glutamine synthetase regulation in the rat brain. *Mol Brain Res* 1994; 26: 123–128.

What is claimed is:

1. A method of treating age related behavioral problems in canines comprising administering an effective amount of adrafinil to a canine in need thereof.

2. A method according to claim 1 wherein treatment with adrafinil improves learning.

3. A method according to claim 1 wherein treatment with adrafinil improves bladder control.

4. A method according to claim 1 wherein treatment with adrafinil improves exploratory behavior.

5. A method according to claim 1 wherein treatment with adrafinil improves memory.

6. A method according to claim 2 wherein treatment with adrafinil improves discrimination learning.

7. A method according to claim 5 wherein treatment with adrafinil improves spatial memory.

8. A method according to claim 5 wherein treatment with adrafinil improves object recognition.

9. A method according to claim 1 wherein the adrafinil is administered at a dose of about 10 to about 50 mg/kg.

10. A method according to claim 1 wherein the adrafinil is administered at a dose of at least 20 mg/kg.

11. A method according to claim 3 wherein the adrafinil is administered at a dose of about 20 to about 40 mg/kg.

12. A method of treating age related behavioral problems in canines as in claim 1, wherein the age related behavioral problems are associated with beta amyloid protein deposits in the brain.

13. A method of claim 12, wherein the beta amyloid protein deposits are within the frontal, and/or temporal lobes of the brain.

14. A method of claim 12 wherein the beta amyloid protein deposits are within the prefrontal cortex and/or entorhinal cortex of the brain.

15. A method of treating age related behavioral problems in canines as in claim 1, wherein said age related behavioral problems are not linked to any other medical condition, and are associated with learning impairment, memory impairment, or both.

16. A method of claim 15, wherein said learning impairment is manifested by difficulty acquiring neuropsychological tasks.

17. A method of claim 15, wherein said memory impairment is manifested by difficulty in performing tasks that include a delay interval.

18. A method of treating age related behavioral problems in canines as in claim 1, wherein said age related behavioral problems are associated with a resting electroencephalogram composed predominantly of delta and theta frequencies.

* * * * *